/

US009387280B2

(12) United States Patent
Brunelle et al.

(10) Patent No.: US 9,387,280 B2
(45) Date of Patent: Jul. 12, 2016

(54) DEVICE FOR SOFT TISSUE REPAIR OR REPLACEMENT

(75) Inventors: John Brunelle, Laguna Beach, CA (US); Al Weinstein, East Wayne, NJ (US)

(73) Assignee: Synovis Orthopedic and Woundcare, Inc., St. Paul, MN (US)

( * ) Notice: Subject to any disclaimer, the term of this patent is extended or adjusted under 35 U.S.C. 154(b) by 1031 days.

(21) Appl. No.: 12/205,260

(22) Filed: Sep. 5, 2008

(65) Prior Publication Data
US 2010/0063599 A1    Mar. 11, 2010

(51) Int. Cl.
| A61F 2/02 | (2006.01) |
| A61B 17/08 | (2006.01) |
| A61L 31/04 | (2006.01) |
| A61L 31/14 | (2006.01) |
| A61F 2/00 | (2006.01) |

(52) U.S. Cl.
CPC ............. *A61L 31/044* (2013.01); *A61L 31/146* (2013.01); *A61F 2/0063* (2013.01)

(58) Field of Classification Search
CPC ............................ A61L 31/146; A61F 2/0063
See application file for complete search history.

(56) References Cited

U.S. PATENT DOCUMENTS

| 4,001,442 A | 1/1977 | Stahlberger et al. |
| 4,280,954 A | 7/1981 | Yannas et al. |
| 4,329,743 A | 5/1982 | Alexander et al. |
| 4,411,027 A | 10/1983 | Alexander et al. |
| 4,427,808 A | 1/1984 | Stöl et al. |
| 4,433,688 A | 2/1984 | Bichon |
| 4,441,215 A | 4/1984 | Kaster |
| 4,488,911 A | 12/1984 | Luck et al. |
| 4,506,672 A | 3/1985 | Bichon |
| 4,512,038 A | 4/1985 | Alexander et al. |
| 4,629,458 A | 12/1986 | Pinchuk |
| 4,772,285 A | 9/1988 | Ksander et al. |
| 4,772,288 A | 9/1988 | Borner et al. |
| 4,842,575 A | 6/1989 | Hoffman, Jr. et al. |
| 4,979,956 A * | 12/1990 | Silvestrini ................. 623/13.11 |

(Continued)

FOREIGN PATENT DOCUMENTS

| EP | 0 943346 | 9/1999 |
| EP | 1493404 | 1/2005 |

(Continued)

OTHER PUBLICATIONS

Bell, et al. in 1979 (Proc. Natn. Acad. Sci. USA, 76, (1274-1278)).

(Continued)

*Primary Examiner* — Todd J Scherbel
(74) *Attorney, Agent, or Firm* — Bret E. Field; Bozicevic, Field & Francis, LLP

(57) ABSTRACT

Disclosed are composite implantable tissue attachment devices comprising a mechanical reinforcing component and a cellular scaffold component. Disclosed devices include a wide, relatively flat portion for supporting long term repair of tissue. Disclosed devices can include a tapered portion at the end of the wide portions that can lead into a narrower elongated extension for aiding in placement of the device during a surgical procedure. The wide portion of the device can provide tensile strength along the longitudinal axis of the device as well as porosity. The wide devices can cover a larger surface area of a delivery site than standard suture. Disclosed materials can be utilized in, e.g., soft tissue repair such as tendon and ligament reconstruction and repair.

42 Claims, 9 Drawing Sheets

(56) References Cited

U.S. PATENT DOCUMENTS

| | | | |
|---|---|---|---|
| 5,104,405 A | 4/1992 | Nimni | |
| 5,108,424 A | 4/1992 | Hoffman, Jr. et al. | |
| 5,171,273 A | 12/1992 | Silver et al. | |
| 5,308,889 A | 5/1994 | Rhee et al. | |
| 5,447,536 A | 9/1995 | Girardot et al. | |
| 5,458,636 A * | 10/1995 | Brancato | 623/23.72 |
| 5,514,181 A | 5/1996 | Light et al. | |
| 5,595,621 A | 1/1997 | Light et al. | |
| 5,711,960 A | 1/1998 | Shikinami | |
| 5,733,337 A | 3/1998 | Carr, Jr. et al. | |
| 5,733,339 A * | 3/1998 | Girardot et al. | 8/94.11 |
| 5,789,465 A | 8/1998 | Harvey et al. | |
| 5,891,167 A | 4/1999 | Totakura | |
| 5,911,951 A | 6/1999 | Girardot et al. | |
| 6,001,895 A | 12/1999 | Harvey et al. | |
| 6,312,474 B1 | 11/2001 | Francis et al. | |
| 6,350,284 B1 | 2/2002 | Törmälä et al. | |
| 6,436,110 B2 | 8/2002 | Bowman et al. | |
| 6,478,825 B1 | 11/2002 | Winterbottom | |
| 6,506,339 B1 | 1/2003 | Girardot et al. | |
| 6,511,511 B1 | 1/2003 | Slivka et al. | |
| 6,521,179 B1 | 2/2003 | Girardot et al. | |
| 6,599,323 B2 | 7/2003 | Melican et al. | |
| 6,599,526 B2 | 7/2003 | Dimitrijevich | |
| 6,623,963 B1 * | 9/2003 | Muller et al. | 435/395 |
| 6,626,950 B2 | 9/2003 | Brown et al. | |
| 6,638,285 B2 | 10/2003 | Gabbay | |
| 6,638,312 B2 * | 10/2003 | Plouhar et al. | 623/23.72 |
| 6,652,594 B2 | 11/2003 | Francis et al. | |
| 6,709,452 B1 | 3/2004 | Välimaa et al. | |
| 6,736,823 B2 | 5/2004 | Darois et al. | |
| 6,746,458 B1 | 6/2004 | Cloud | |
| 6,790,213 B2 | 9/2004 | Cherok et al. | |
| 6,827,743 B2 | 12/2004 | Eisermann et al. | |
| 6,852,330 B2 | 2/2005 | Bowman et al. | |
| 6,884,428 B2 | 4/2005 | Binette et al. | |
| 6,946,003 B1 | 9/2005 | Wolowacz et al. | |
| 6,977,231 B1 | 12/2005 | Matsuda | |
| 6,989,034 B2 | 1/2006 | Hammer et al. | |
| 6,991,652 B2 | 1/2006 | Burg | |
| 7,011,688 B2 | 3/2006 | Gryska et al. | |
| 7,112,417 B2 | 9/2006 | Vyakarnam et al. | |
| 7,160,333 B2 | 1/2007 | Plouhar et al. | |
| 7,192,604 B2 | 3/2007 | Brown et al. | |
| 7,217,294 B2 | 5/2007 | Kusanagi et al. | |
| 7,338,531 B2 | 3/2008 | Ellis et al. | |
| 7,341,601 B2 | 3/2008 | Eisermann et al. | |
| 7,569,233 B2 * | 8/2009 | Malaviya et al. | 424/422 |
| 7,799,089 B2 * | 9/2010 | Plouhar et al. | 623/23.72 |
| 8,092,529 B2 * | 1/2012 | Malaviya et al. | 623/14.12 |
| 2003/0212456 A1 * | 11/2003 | Lipchitz et al. | 623/13.17 |
| 2004/0267362 A1 * | 12/2004 | Hwang et al. | 623/13.15 |
| 2005/0033362 A1 | 2/2005 | Grafton | |
| 2005/0070930 A1 | 3/2005 | Kammerer | |
| 2005/0123581 A1 * | 6/2005 | Ringeisen et al. | 424/423 |
| 2005/0249771 A1 * | 11/2005 | Malaviya et al. | 424/423 |
| 2007/0150063 A1 * | 6/2007 | Ruberte et al. | 623/17.16 |
| 2008/0027542 A1 | 1/2008 | McQuillan et al. | |
| 2008/0147098 A1 * | 6/2008 | Trieu | 606/151 |
| 2009/0018655 A1 * | 1/2009 | Brunelle et al. | 623/13.19 |
| 2009/0137862 A1 * | 5/2009 | Evans et al. | 600/37 |
| 2009/0306776 A1 * | 12/2009 | Murray | 623/13.12 |

FOREIGN PATENT DOCUMENTS

| | | |
|---|---|---|
| EP | 1 504773 | 2/2005 |
| WO | WO 8500511 | 2/1985 |
| WO | WO0016822 | 3/2000 |
| WO | WO 2006062342 | 6/2006 |
| WO | WO2007092464 | 8/2007 |

OTHER PUBLICATIONS

Nimni et al., J. Biol. Chem. 243:1457-1466 (1968).
Nimni et al., J. Biomed. Mater. Res. 21:741-771 (1987).
Woodroof, E. A., J. Bioeng. 2:1 (1978).
Mazzocca, et al, *Tendon and Bone Responses to a Collagen-Coated Suture Material*, J Shoulder Elbow Surg, Sep./Oct. 2007.

* cited by examiner

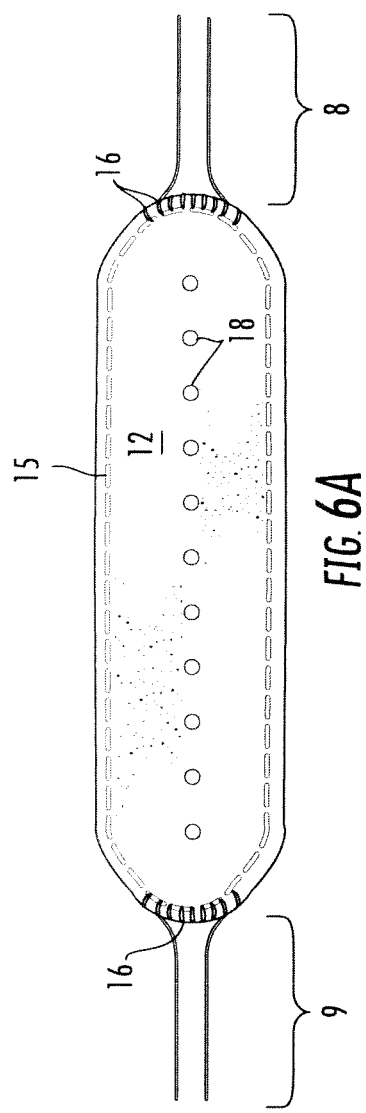
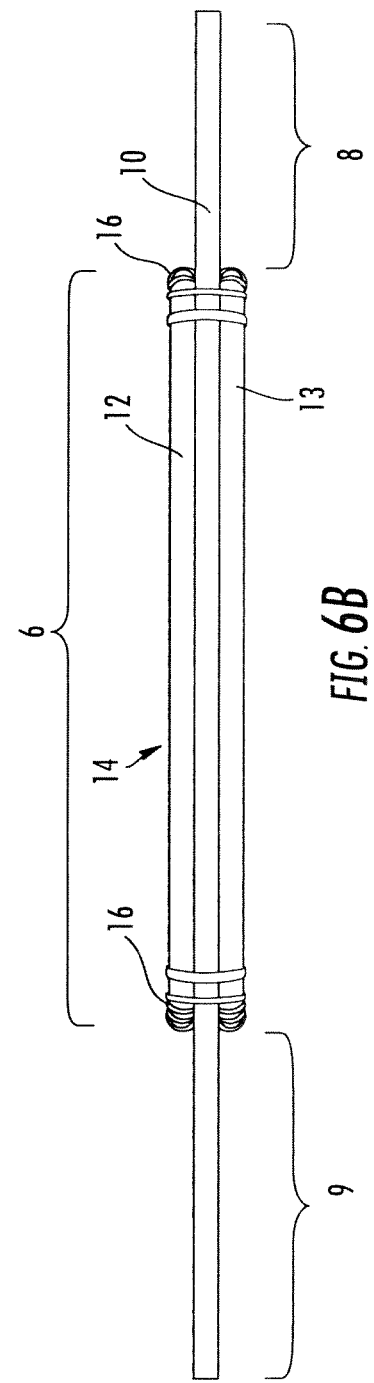
FIG. 6A
FIG. 6B

DEVICE FOR SOFT TISSUE REPAIR OR REPLACEMENT

BACKGROUND

Surgical repair of damaged soft tissue is a procedure that is being carried out with increasing frequency. The most common method for soft tissue repair is to suture together the torn or damaged portions of the affected tissue. This technique involves the approximation of damaged soft tissue portions or the approximation of damaged soft tissue to a bony insertion site where the suture may be affixed to an anchor.

This relatively simple method carries several drawbacks, however. For instance, healing is dependent on biological interaction and contact that is facilitated by the mechanical fixation. Should complete healing not occur the integrity of the repair becomes solely dependent on the mechanical suture fixation, which can deteriorate over time. Additionally, most failures in soft tissue repair are due at least in part to one or more of poor tissue quality, poor vascular supply and poor tissue contact with the vascular supply, technique variation, and inherent dynamic functional nature of the repair sites. For instance, in rotator cuff repair failure rates are reported to be from 10 to 90%. These failures primarily occur at the interface between the host tissue and the tissue fixation device (typically suture) where the mechanism of failure is primarily suture pull out.

In an attempt to maximize biological contact and increase the likelihood of healing, multiple sutures and sometimes multiple anchors as well, have been arranged at the affected site so as to distribute load evenly across the repair site and maximize contact at the interface of the tissues. However, load distribution is still limited and concentrated at the sutures, and suture can pull through the tissue under heavy or cyclic load. Moreover, such processes require increased knot tying and increased time, which can contribute to the increased possibility of development of complications.

In addition, these repair techniques are strictly mechanical and attempt to merely restore anatomy and mechanical function. As a result, more recent advances have led to the development of tissue augmentation products that can be affixed to the damaged and/or surrounding tissues to facilitate healing, but these are not indicated for primary mechanical repair and aim merely to restore tissue mass at a surgical site. Procedures that require both mechanical fixation and biologic augmentation can be carried out, but these procedures are time consuming in that they require both steps separately, i.e., the mechanical fixation through suturing as well as a separate tissue augmentation process, again leading to increased time for completion and associated increased chance of development of complications What are needed in the art are implantable materials that can provide improved mechanical repair of soft tissue injuries. What are also needed in the art are materials that can provide for both mechanical repair and tissue augmentation in a single step procedure.

SUMMARY

According to one embodiment, disclosed is a composite implantable tissue attachment device that can be attached to tissue during a surgical procedure. An attachment device as disclosed herein can include a mechanical reinforcing component and a cellular scaffold component affixed thereto. A tissue attachment device as disclosed herein can define a length, width and depth. In addition, at least a portion of the length of the device can define a width that is at least about 1 millimeter across, and this width can be greater than the depth of the device along this length. A device can also include narrower sections, for instance narrower ends for instance to aid in delivery of a device to a repair site.

In one embodiment, a mechanical reinforcing component of a tissue attachment device can have porosity that can differ at different areas of the component. For instance, one area of a mechanical reinforcing component can define porosity suitable for cellular passage and another area of the component can define little or no porosity. In general, a device can exhibit tensile strength suitable for surgical repair of soft tissues. In one preferred embodiment, a device can include multiple cellular scaffold components, for instance a collagen scaffold affixed to either side of all or a portion of a mechanical reinforcing component of a device, so as to form a sandwich-type composite device.

Also disclosed are methods for forming disclosed devices. For example, a mechanical reinforcing component of a tissue attachment device can be a fibrous device and a formation method can include attaching fibers to one another to form the component having the desired geometry. A cellular scaffold component can then be attached to the mechanical reinforcing component, for instance by suturing.

Also disclosed are methods for repairing tissue utilizing disclosed devices. For example, a method can include passing a first length of an implantable tissue attachment device as described herein through a first tissue and then attaching the device to a second tissue. The first and second tissues can be, for example, different areas of a single tissue or two different tissues, e.g., a tendon and a bone.

BRIEF DESCRIPTION OF THE FIGURES

A full and enabling disclosure of the present subject matter, including the best mode thereof, to one of ordinary skill in the art, is set forth more particularly in the remainder of the specification, including reference to the accompanying figures, in which:

FIG. 6 illustrates a top view (FIG. 6A) and a side view (FIG. 6B) of a composite implantable device as described herein including two cellular scaffold portions, one on either side of a wide portion of a base mechanical reinforcing component;

Figure 1:
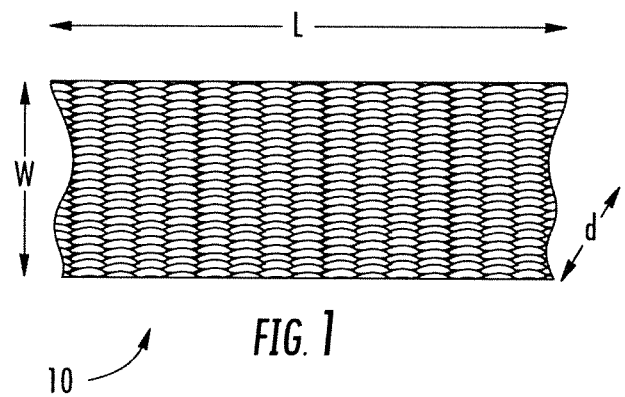
FIG. 1 illustrates one embodiment of a mechanical reinforcing component of a composite implantable device as described herein.

Repeat use of reference characters in the present specification and drawings is intended to represent the same or analogous features or elements of the present disclosure.

DETAILED DESCRIPTION

Reference will now be made in detail to various embodiments of the disclosed subject matter, one or more examples of which are set forth below. Each embodiment is provided by way of explanation of the disclosed subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used with another embodiment to yield a still further embodiment.

Presently disclosed subject matter is generally directed to implantable devices as may be beneficially utilized in tissue repair protocols such as, without limitation, tissue replacement, stabilization, reconstruction, and the like. More specifically, disclosed devices can be affixed to one or more tissues. For example, an implantable device as disclosed herein can be attached to one or more tissues through a stitching mechanism. Also disclosed herein are methods for forming the devices as well as methods for using the devices.

At least a portion of a disclosed device can be relatively wide, e.g., wider than materials that have been commonly utilized for soft tissue repair in the past. As a result, disclosed devices can cover a larger surface area of a tissue to which they are applied. This greater area of contact can distribute the load of the repair materials over a larger area of the tissue to which it is affixed and prevent pullout and repetition of or additional damage to a site. In addition, the greater area of contact between a device and tissue to which it is applied can increase area of contact between tissues that are approximated during the procedure, e.g., can better restore the natural tendon to bone footprint in a tendon repair procedure. Accordingly, utilization of disclosed devices can improve biological interaction between approximated tissues and encourage healing of the tissues, for instance through enhanced contact area with the vascular supply due to both enhanced contact area and improved load distribution. In addition, devices as disclosed herein can provide improvements in maneuverability, strength, tenacity, and/or immediate reinforcement ability of suture-type materials. Disclosed devices also combine these capabilities with the tissue regeneration and excellent long-term healing characteristics of cellular scaffold materials.

Implantable devices as disclosed herein can, in general, be utilized in any fashion as is known for suture materials. In contrast to suture, however, disclosed devices define a shape more conducive to a wide variety of repair and reconstructive procedures. In particular, disclosed devices can have a width that can improve contact between the device and tissue to which it is applied. In addition, a cellular scaffold component of disclosed devices can be less abrasive on surrounding tissue than suture, reducing the likelihood that a device will pull out of the tissue. Implantable devices as disclosed herein can be utilized in any fashion as is known for surgical tapes, surgical meshes, and the like, including tissue fixation devices.

FIG. 1 illustrates a mechanical reinforcing component 10 as may be utilized as a portion of a composite device as disclosed herein. As can be seen, component 10 defines a width W, a depth D, and a length L, a portion of which is illustrated in FIG. 1. The width W of the widest portion of a device can generally be greater than that of standard suture. For instance at least a portion of a device as disclosed herein can include a width W greater than about 1 millimeter (mm). For example, a device can include a portion having a width W between about 1 and about 2 mm, in one embodiment, or between about 2 and about 10 mm, in another embodiment, or between about 10 and 20 mm in another embodiment.

The depth D of a mechanical reinforcing component 10 can vary. For instance, while the depth of a mechanical reinforcing component can generally be less than a wide portion W of the device, as is illustrated in FIG. 1, this is not a requirement of the disclosed subject matter. In general, however, the depth D of a component 10 can provide a composite device with a relatively low functional profile, so as to minimize interference of a composite device with surrounding structures during delivery and following implantation. In addition, the depth D of a mechanical reinforcing component can provide a composite device with flexibility such that it can lie across the contour of a tissue following implantation. The length L of a mechanical reinforcing component can also vary, and can generally be optimized depending upon the nature of the application for which any particular device design is intended.

A mechanically reinforcing component can be formed from any of a wide variety of biocompatible materials, as well as combinations of materials. For instance, a component 10 can be formed from any of a wide variety of biocompatible substituted or unsubstituted polymeric materials including, without limitation, polyketones such as polyetherether ketone; polyesters such as high tenacity polyester; polyethylene such as ultra high molecular weight polyethylene; absorbable polymers including those based upon polylactic acid and/or polyglycolic acid; natural polymers such as silk; and the like. A component 10 can also be formed from any of a wide variety of metallic materials, including, without limitation, stainless steel, titanium, and the like.

Similarly, a mechanical reinforcing component 10 can be formed according to any suitable formation process that can provide a component and composite device incorporating the component including the desired geometry and at a suitable longitudinal tensile strength. In particular, disclosed devices can exhibit a tensile strength, alternatively referred to herein as tensile failure load, greater than about 20 Newtons, for instance between about 20 and 100 Newtons (N), or greater in other embodiments, for instance greater than about 200N. In other embodiments, a device can exhibit a tensile strength of up to about 300N, 500N, 1000N, 2000N, and 5000N. In another embodiment, a woven component 10 can be formed having different quantities of yarn ends throughout the component so as to achieve a particular tensile strength of the device according to methods as are generally known in the art. For instance, with reference to FIG. 2, an increase in the total number of yarn ends introduced into the weave can increase the tensile strength of the woven component 10 and hence the composite device of which it is a part.

In one preferred embodiment, a mechanical reinforcing component 10 can include fibrous materials. For instance, a component 10 can include mono- or multi-filament fibers or yarns. Multi-filament fibers or yarns can generally include between about 5 and about 100 individual filaments of the same or different materials, usually including some twist in the yarn. Moreover, yarns can include multi-component fibers including core/sheath fibers, islands-in-the-sea fibers, braided fibers, and so on, as well as fibers including adjacent lengths of different materials. Fibers and filaments as may be utilized herein can be absorbable or non-absorbable and can define any cross-sectional area.

For example, mechanical reinforcing component 10 can be a woven, nonwoven, or knit fabric. The term 'fabric' as utilized herein generally refers to any generally planar textile structure produced by the attachment of fibers to one another via the interlacing and/or adhesion of yarns, multi-filament fibers, monofilament fibers, or some combination thereof. Accordingly, a component 10 can include fibers in a predetermined, organized, and interlaced pattern, herein referred to as a woven fabric (i.e., a fabric formed according to a weaving and/or knitting process), or optionally can include fibers in a random pattern (a nonwoven fabric). Mechanical reinforcing component 10 can be fabricated from yarns and fibers of different materials in any combination, for example a non-absorbable yarn woven with an absorbable yarn. Additionally, mechanical reinforcing component 10 can be fabricated using fibers and another material, for example, a yarn interwoven with a suture. Fibers can include synthetic and/or natural polymers, as desired. For example, fibers can include any of a variety of known absorbable polymers.

A woven component 10 can be formed according to any textile formation process utilizing any weaving, knitting, and/or braiding textile formation systems and devices as are generally known in the art. For example, a woven component 10 can include a weave structure of up to 100 picks per inch and about 100 ends. In addition, any weave pattern or combination thereof can be utilized. For example, weave patterns such as plain, twill and satin that are well known in the art can be utilized alone or in combination in the disclosed structures.

A nonwoven fabric component 10 can be formed according to any suitable formation process as in generally known in the art. For example, following formation, a plurality of fibers can be randomly laid on a traveling formation fabric according to any known process and bound to one another utilizing an adhesive, applied heat, applied pressure, chemical agents or some combination thereof. Suitable biocompatible adhesives are generally known in the art can be applied during the fiber formation process or during the web-formation process, as desired.

By way of example, fibers included in a component 10 can have a linear density greater than about 100 decitex, for instance between about 100 and about 1000 decitex, for instance between about 250 and about 300 decitex. In other applications a portion of fibers included in a component 10 can have a lower linear density, for instance greater than about 10 decitex, or between about 1 decitex and about 100 decitex, for instance between about 50 and about 100 decitex. For multi-filament fibers, each fiber can contain between about 1 and about 30 filaments, for instance between about 10 and about 20 filaments, or about 15 filaments, in another embodiment. Variation in linear density can be developed with use of different materials, as well as the quantity of filaments per fiber and filament linear density.

Figure 2:
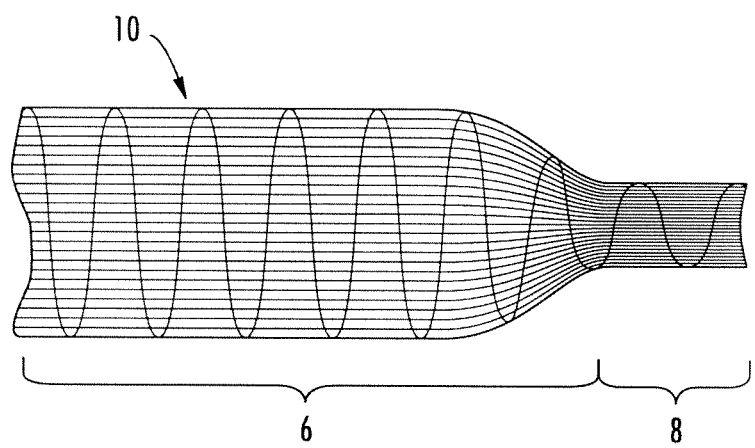
FIG. 2 illustrates another embodiment of a mechanical reinforcing component of a composite implantable device as described herein including a tapered end.

A device or a portion thereof can define porosity that, unless otherwise noted, is described herein in terms of average pore size. For instance, in one embodiment, a mechanical reinforcing component 10 of a device can define porosity favorable for cellular passage. In one embodiment, a component can define a porosity that is appropriate to allow fibrous tissue ingrowth to the component and/or device. By way of example, a mechanical reinforcing component 10 can define a porosity between 0 (i.e., no porosity) and about 1000 micrometers (μm) in average pore size, for instance between about 100 μm and about 500 μm, in one embodiment, or between about 200 μm and about 400 μm, in another embodiment. Moreover, as discussed above, different regions of a component 10 can describe different characteristics. For example, and with reference to FIG. 2, area 8 can define little or no porosity, while area 6, the wider portion of the component 10, can define a larger porosity. For instance area 6 can define a porosity having an average pore size of up to about 100 μm, in one embodiment. In another embodiment, area 6 can define a porosity having an average pore size of between about 100 μm and about 500 μm.

A woven component can be formed having different picks per inch (ppi) and/or total yarn ends across the length of the component so as to vary porosity of the component, according to methods as are generally known in the art.

Individual components of devices as disclosed herein can be formed according to any suitable formation process. In particular, it should be understood that while disclosed devices can include woven fibrous materials in one preferred embodiment, disclosed subject matter is by no means limited to woven materials. For instance, in addition to woven and nonwoven textile materials, components of devices as described herein can be formed according to any suitable formation process that can provide an implantable device defining disclosed characteristics, for instance disclosed geometries and/or strength characteristics. For instance, individual components of disclosed biocompatible devices can be formed according to processes including, but not limited to, injection molding, extrusion, machining, solvent molding, spray coating, fused deposition modeling, selective laser sintering, stereolithography, and the like, as well as combinations of formation processes, according to methods as are generally known to one of skill in the art.

The overall geometry of a device can vary across a dimension of the component. For instance, and with reference to FIG. 2, a relatively wide portion 6 of a mechanical reinforcing component 10 of a device can taper at an end to form a narrower portion 8. Narrow portion 8 can be an elongated portion that can, for instance, facilitate delivery and/or placement of the device at a repair site. Addition of an elongated narrow portion 8 to a device can be particularly beneficial in certain application techniques, such as those involving arthroscopy. Portion 8 can be of any suitable cross-sectional geometry, e.g., flat, round, square, tubular, etc.

The end of portion 6 can be tapered, for instance through a gradual adjustment of equipment process parameters, to form narrower portion 8. The entirety of the fibers of portion 6 can extend to portion 8, so as to maintain a suitable longitudinal tensile strength in component 10. In one embodiment, the yarn ppi introduced into portion 8 can be decreased from that of portion 6 so as to increase flexibility of portion 8. This can be advantageous when utilizing portion 8 during delivery of a device, particular during arthroscopic delivery.

The relationship in width between portion 6 and portion 8 can be as desired. For instance, portion 8 can be less than about 90%, less than about 60%, less than about 50%, or less than about 30% of the width of portion 6, in various embodiments. Alternatively, portion 6 and portion 8 can be about the same width.

Figure 3:
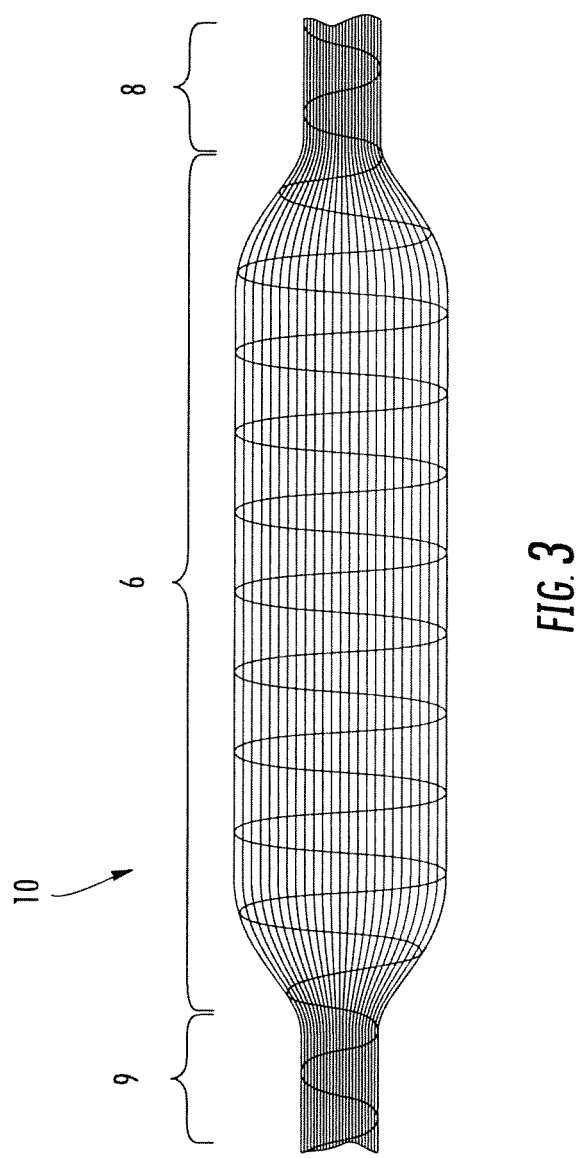
FIG. 3 illustrates another embodiment of a mechanical reinforcing component of a composite implantable device as described herein including two elongated extensions.

A mechanical reinforcing component can have multiple portions of varying width. For example, FIG. 3 illustrates one embodiment of a component 10 including wide portion 6 and two narrow portions 8, 9, one on either end of wide portion 6.

Figure 4:
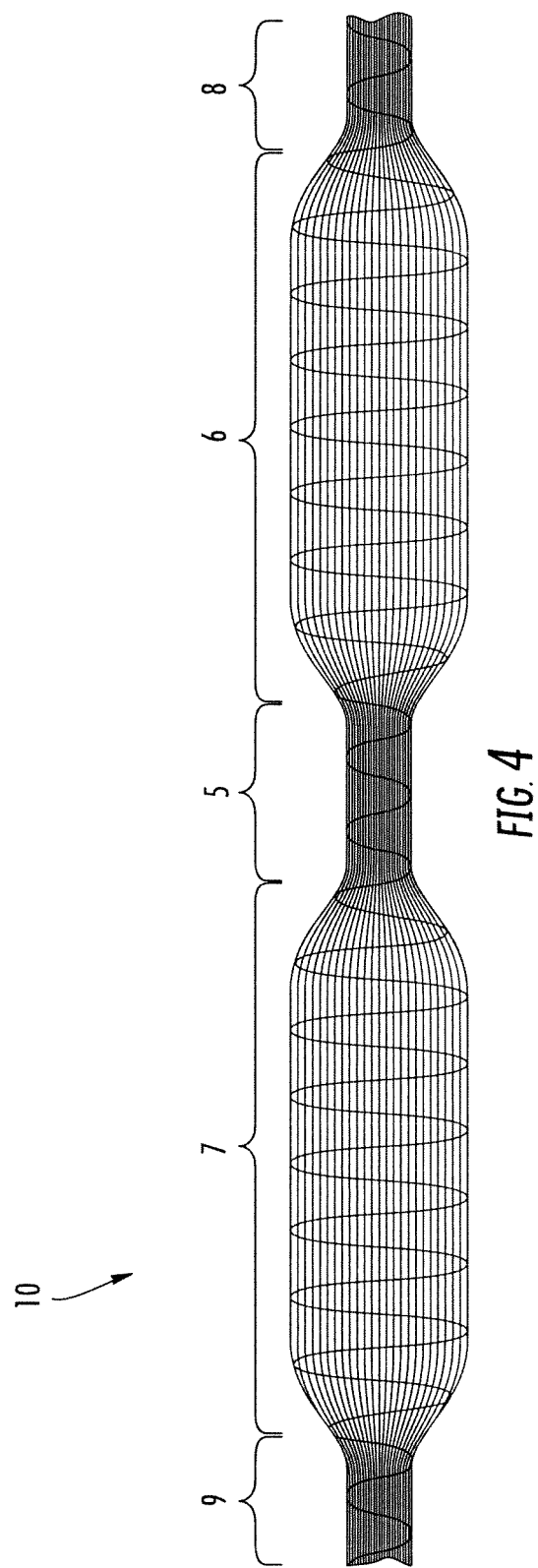
FIG. 4 illustrates another embodiment of a mechanical reinforcing component of an implantable device as described herein including two wider and three narrower sections.

FIG. 4 illustrates another embodiment of a mechanical reinforcing component 10 including a first wide portion 6 and a second wide portion 7 with a neck 5 separating the two. In this particular embodiment, the component 10 also includes terminal end portions 8, 9, as described previously. Addition of a neck 5 between wider portions 6, 7 of a component can assist in proper location of a device at a delivery site, e.g., centering of a device, as well as providing other benefits, discussed at more length below. A device as encompassed herein can include additional sections that vary from one another according to width, length, and/or depth from one another as would be understood and well within the abilities of one of skill in the art.

An implantable composite device as disclosed herein can include a mechanical reinforcing component as described above in conjunction with a scaffolding component. As utilized herein, the term 'scaffold' can generally refer to biocompatible materials that can facilitate cellular growth and development when located in proximity to living cells. Scaffold materials encompassed herein include those designed for in vivo, ex vivo, and/or in vitro use. In general, scaffold materials can describe a physical structure that can allow cellular ingrowth to the scaffold. For example, a scaffold can include macro- and/or microporosity that can allow cellular and/or nutrient propagation throughout all or a portion of the scaffold. In one embodiment, a scaffold can include a matrix with a mesh size, $\xi$, or a pore size, $\rho$, which can allow cellular propagation, nutrient propagation, and/or ingrowth throughout the matrix. Scaffolding materials as may be included in disclosed devices can include those disclosed in U.S. patent application Ser. No. 11/777,733, to Brunelle, et al., incorporated herein in its entirety by reference.

Scaffolds encompassed by the disclosed subject matter can include one or more materials that can encourage the growth and development of a cellular construct. For instance, a scaffold can include one or more synthetic or natural biocompatible polymers that have been shown to promote wound healing. Biocompatible synthetic polymers as may be utilized in forming a scaffold can include, e.g., polyurethanes, polyesters, polyethylenes, silicones, polyglycolic acid (PGA), polylactic acid (PLA), copolymers of lactic and glycolic acids (PLGA), polyanhydrides, polyorthoesters, and the like. A scaffold can include one or more natural polymers including, e.g., chitosan, glycosaminoglycans, and collagen.

In one preferred embodiment, a scaffold can contain collagen. Collagen is the most abundant fibrous structural protein found in mammals and has been shown to exhibit many desirable qualities in scaffolding materials. For example, in addition to good bioaffinity and histocompatibility, wound healing cells such as fibroblasts have been shown to have good affinity for collagen, and the presence of collagen in a scaffold can encourage and promote cell growth and differentiation of the tissues/cells associated with the scaffold. In addition, collagen can act as a conduit for healthy cells and nutrients from surrounding healthy tissue such as healthy tendon or bleeding bone to the repair site.

Collagen encompassed by the present disclosure can include any collagen type or combination of collagen types. For instance, a collagen-containing scaffold can include any one or combination of the currently known 28 types of collagen. Typically, a collagen-containing scaffold can include at least some type I and/or type II collagen, as types I and II collagen are the most abundant types of collagen, and the introduction of organized type I collagen has been shown to be beneficial in cellular integration and tendon remodeling. However, it should be understood that the presence of either of any specific collagen type is not a requirement in a collagen-containing scaffold as disclosed herein.

A collagen-containing scaffold can be derived of any suitable collagen source and formed according to any suitable method as is understood by one of ordinary skill in the art. For example, a collagen-based scaffold can include natural collagen-containing tissues that can be allograft, autograft, and/or xenograft tissues. Natural collagen-containing tissues that can be used to form a scaffold can include, without limitation, soft tissues including ligament, tendon, muscle, dura, pericardium, fascia, peritoneum, and the like and can be derived from any host source (*human, equine, porcine, bovine,* etc.).

A natural tissue scaffold can be processed to remove some or all of the cellular components of the tissue. For example, a tissue for use as a scaffold can be air-dried or lyophilized to kill cells contained therein. Thermal shock, sonication or ultrasound treatment, changes in pH, osmotic shock, mechanical disruption, or addition of toxins can also induce cell death or apoptosis. Other treatments to de-cellularize or denature the tissue are possible using radiation, detergents (e.g., sodium dodecyl sulfate (SDS)), enzymes (RNAase, DNAase), or solvents (alcohol, acetone, or chloroform). These techniques are only some of the examples of techniques to de-cellularize, denature or chemically modify all or part of the tissue and are not meant to limit the scope of the disclosure. For example, methods of de-cellularizing can utilize, for example, enzymes such as lipases combined with other enzymes and, optionally, detergents. Treatment with hypotonic and/or hypertonic solutions, which have non-physiological ionic strengths, can promote the de-cellularization process. These various de-cellularization solutions generally are suitable as treatment solutions. Proteases also can be used effectively to de-cellularize tissue. The de-cellularization can be performed in stages with some or all of the stages involving differential treatments. For example, a mixture of proteases, nucleases and phospholipases can be used in high concentrations to de-cellularize a tissue.

Collagen-containing materials can be processed according to any suitable methods during a collagen scaffold preparation process. For instance, a collagen-containing scaffold can be derived from reconstituted collagen. The capability of utilizing reconstituted collagen to form a scaffolding material was first published by Bell, et al. in 1979 (Proc. Natn. Acad. Sci. USA, 76, 1274-1278, incorporated herein by reference). In general, methods for forming scaffolds from reconstituted collagen include extraction and purification of collagen(s) from connective tissues by solubilization that can be acidic, alkaline, neutral and/or enzymatic in nature. The extracted collagen can be broken down to monomeric and/or oligomeric level and stored as a powder or liquid. Upon rehydration, a solution can form that can be molded and crosslinked via chemical or physical methods to form a scaffold.

Variations and improvements upon these processes can be utilized. For example, U.S. Pat. No. 6,623,963 to Muller, et al., incorporated herein by reference, describes a method for forming a scaffold that includes solubilizing animal cartilage tissue by physical and/or chemical treatment processes that include treatment with various buffers to remove impurities and to separate the solid and liquid phases; physical treatment to separate solid and liquid phases, such as by centrifugation; and treatment with a proteolytic enzyme that breaks the crosslinking of the collagen in its telopeptide region into its virtually non-crosslinked, atelocollagen, triple helix form. The collagen thus obtained is then reconstituted, i.e., the non-crosslinked, atelocollagen form of collagen reestablishes its crosslinking between the variable regions along the collagen molecule, including some remaining residues in the telopeptide region. As a result, the solubilized collagen loses its liquid or gel-like consistency and becomes more rigid with a higher degree of structural integrity such that it may be utilized as a scaffold.

U.S. Pat. No. 4,488,911 to Luck et al., incorporated herein by reference, describes the formation of collagen fibers free of the immunogenic, telopeptide portion of native collagen. The telopeptide region provides points of crosslinking in native collagen. Specifically, collagen obtained from tendons, skin, and connective tissue of animals, such as a cow, is dispersed in an acetic acid solution, passed through a meat chopper, treated with pepsin to cleave the telopeptides and solubilize the collagen, precipitated, dialyzed, crosslinked by addition of formaldehyde, sterilized, and lyophilized. The disclosed method can obtain the atelocollagen form of collagen, free from non-collagen proteins, such as glycosaminoglycans and lipids. Further, the collagen may be used as a gel to make, for example, a membrane, film, or sponge and the degree of crosslinking of the collagen can be controlled to alter its structural properties.

Of course, the above described methods are merely embodiments of processing as may be carried out in forming a collagen-containing scaffold as may be utilized in forming a composite device as disclosed herein and the present disclosure is in no way limited to these embodiments. Many other processing methods and scaffolds formed thereby are known to those of ordinary skill in the art and thus are not described at length herein, any of which may be utilized according to the disclosure.

Moreover, the presently disclosed subject matter is not limited to collagen scaffolds. For instance, in one embodiment, a scaffold can include or be formed entirely of a non-collagen hydrogel matrix. Hydrogel scaffolds are known in the art and are generally defined to include polymeric matrices that can be highly hydrated while maintaining structural stability. Suitable hydrogel scaffolds can include non-crosslinked and crosslinked hydrogels. In addition, crosslinked hydrogel scaffolds can optionally include hydrolyzable portions, such that the scaffold can be degradable when utilized in an aqueous environment. For example, in one embodiment, a scaffold can include a cross-linked hydrogel including a hydrolyzable cross-linking agent, such as polylactic acid, and can be degradable in an aqueous environment.

Hydrogel scaffolds can include natural polymers such as glycosaminoglycans, polysaccharides, proteins, and the like, as well as synthetic polymers, as are generally known in the art. A non-limiting list of polymeric materials that can be utilized in forming hydrogel scaffolds, in addition to collagen, previously discussed, can include dextran, hyaluronic acid, chitin, heparin, elastin, keratin, albumin, polymers and copolymers of lactic acid, glycolic acid, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins peptides and polysaccharides, and the like.

Hydrogel scaffolds can be formed according to any method as is generally known in the art. For instance, a hydrogel can self-assemble upon mere contact of the various components or upon contact in conjunction with the presence of particular external conditions (such as temperature or pH). Alternatively, assembly can be induced according to any known method following mixing of the components. For example, step-wise or chain polymerization of multifunctional monomers or macromers can be induced via photopolymerization, temperature dependent polymerization, and/or chemically activated polymerization. Optionally, a hydrogel can be polymerized in the presence of an initiator. For example, in one embodiment, a hydrogel scaffold can be photopolymerized in the presence of a suitable initiator such as Irgacuree or Darocur® photoinitiators available from Ciba Specialty Chemicals. In another embodiment, a cationic initiator can be present. For example, a polyvalent elemental cation such as $Ca^{2+}$, $Mg^{2+}$, $Al^{3+}$, $La^{3+}$, or $Mn^{2+}$ can be used. In another embodiment, a polycationic polypeptide such as polylysine or polyarginine can be utilized as an initiator.

A scaffold may be processed as desired prior to forming a composite device. For instance, a natural or reconstituted tissue can be stabilized through crosslinking. Generally, a stabilization process operates by blocking reactive molecules on the surface of and within the scaffold, thereby rendering it substantially non-antigenic and suitable for implantation. In 1968, Nimni et al. demonstrated that collagenous materials can be stabilized by treating them with aldehydes. (Nimni et al., J. Biol. Chem. 243:1457-1466 (1968).) Later, various aldehydes were tested and glutaraldehyde was shown to be capable of retarding degeneration of collagenous tissue. (Nimni et al., J. Biomed. Mater. Res. 21:741-771 (1987); Woodroof, E. A., J. Bioeng. 2:1 (1978).) Thus, according to one embodiment, a glutaraldehyde stabilization process as is generally known in the art may be utilized in forming a scaffold (see, e.g., U.S. Pat. No. 5,104,405 to Nimni, which is incorporated herein by reference).

A glutaraldehyde process is only one potential processing method, however, and a scaffold material processed according to any other method as is known in the art may alternatively be utilized. For example, a scaffold material as may be utilized in a disclosed composite device can be stabilized according to a physical crosslinking process including, without limitation, radiation treatment, thermal treatment, electron beam treatment, UV crosslinking, and the like.

In one preferred embodiment, a scaffold can be processed according to a non-glutaraldehyde crosslinking process. For example, non-glutaraldehyde crosslinking methods as disclosed in U.S. Pat. Nos. 5,447,536 and 5,733,339 to Girardot, et al., both of which are incorporated herein by reference, can be utilized. According to one such embodiment, a collagen-containing scaffold can be crosslinked via formation of amide linkages between and within the molecules of the scaffold. For instance, di- or tri-carboxylic acids and di-or tri-amines of about six to eight carbon atoms in length can be used in a sequential manner to form amide crosslinks.

Optionally, a scaffold can be formed to include additional materials. For instance, cellular materials can be retained in or loaded into a scaffold. For example, chondrocytes and/or fibroblasts can be retained in a natural tissue scaffold or loaded into a scaffold prior to implantation. In one embodiment, a scaffold can be seeded with cells through absorption, cellular migration, physical cyclic loading, and scaffold tensioning, optionally coupled with application of pressure through simple stirring, pulsatile perfusion methods or application of centrifugal force. In general, cell seeding can usually be carried out following combination of a scaffold with the other components of the device, described in more detail below.

Other materials as may be incorporated into disclosed composite devices via a scaffold can include any other additive as is generally known in the art. For instance, biologically active agents such as growth factors, antibiotics, extra cellular matrix components, or any other chemical or biological agent as may be beneficially incorporated into a scaffold is encompassed by the presently disclosed subject matter. Additional materials can be loaded into a scaffold, applied to a surface of a scaffold, or combined with another component of a device, as desired.

Figure 5:
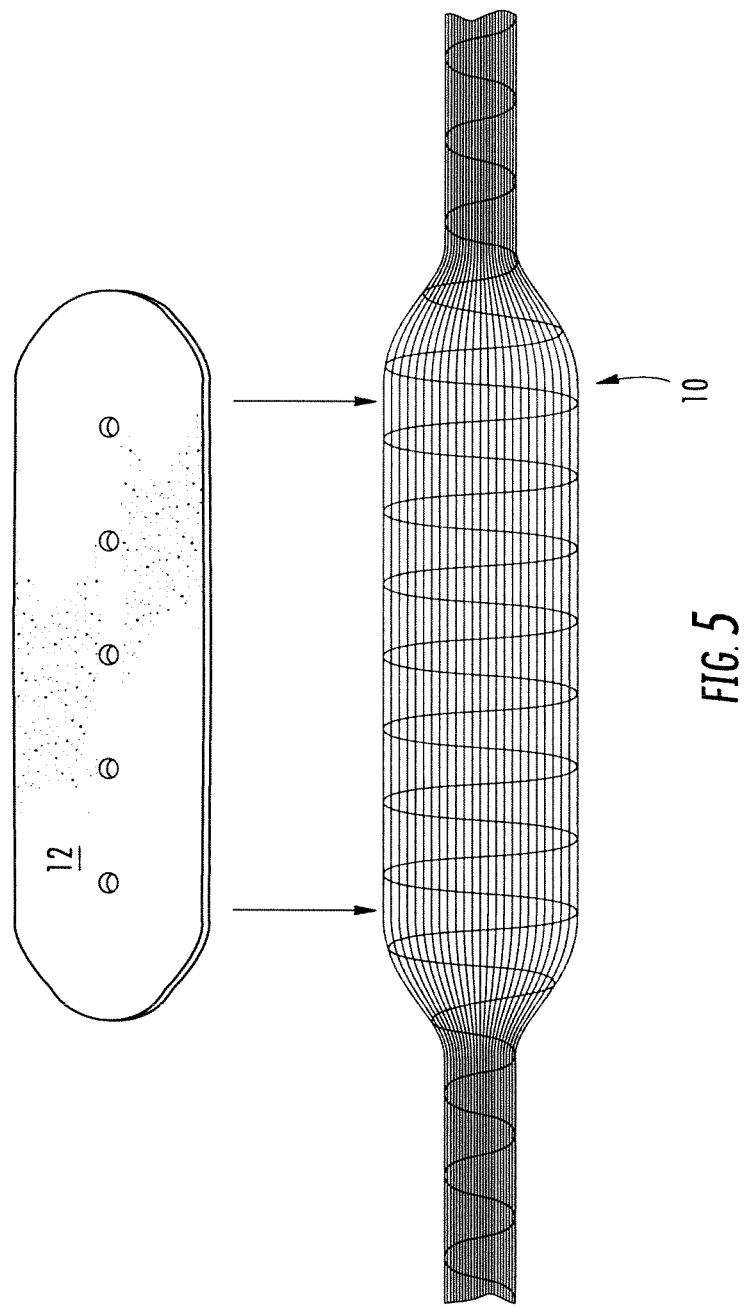
FIG. 5 illustrates a reinforcing mechanical component and a cellular scaffold component of an implantable device as described herein.

In forming a composite implantable device, a scaffold can be attached to a mechanical reinforcing component. For instance, and with reference to FIG. 5, a scaffold 12 can be shaped, for instance through laser cutting of a larger material, so as to correspond in shape to a surface of a component 10, as described above. Scaffold 12 can then be attached to component 10 according to any suitable attachment methods, generally while maintaining tautness in scaffold 12.

For instance, and with reference to FIG. 6, a composite device 14 is illustrated in a top view (FIG. 6A) and a side view (FIG. 6B). Composite device 14 includes a first scaffold 12 and a second scaffold 13 located on either side of a component 10. As can be seen, first scaffold 12 and second scaffold 13 correspond in size and shape to wide portion 6 of component 10 such that following attachment, narrow portion 8 and narrow portion 9 of component 10 extend from wide portion 6 and the scaffolds 12, 13 attached thereto.

In this particular embodiment, scaffolds 12, 13 are secured to component 10 with a series of stitches 15. For instance, one or more scaffolds and one or more mechanical reinforcing components can be sewn together with a suture material. Any suture material as is known in the art can be utilized. Suture material for an implantable device can be absorbable or non-absorbable, as desired. Suture can be of any size (e.g., from #11-0 up to #5 in size), suture can be multifilament and braided or twisted, or can be mono-filament. Suture can be sterile or non-sterile, of natural, synthetic, or a combination of materials. In one embodiment, suture material can be coated. Typical coatings can include, for example, collagen, magnesium stearate, PTFE, silicone, polybutilate, and antimicrobial substances.

A large variety of suitable suture is known to those of skill in the art and can include, without limitation, collagen, catgut, polyglycolic acid, polyglactin 910, poliglecaprone 25, polydioxanone, surgical silk, surgical cotton, nylon, polybutester, polyester fibers, polyethylene fibers, polypropylene fibers, and the like. For instance, polyethylene suture such as co-braided polyethylene suture can be utilized.

A composite device can include any of a variety of enhancements, as desired. For instance, in the embodiment illustrated in FIG. 6, a series of additional edge stitches 16 can be added at the ends of scaffolds 12, 13. Additional edge stitches 16 can increase securement of the components of device 14 as well as decrease the overall profile of device 14 at the end points of the scaffolds 12, 13, which may aid in delivery of a device 14 in those embodiments in which all or a part of device 14 is pulled through a tissue, for instance a tendon portion.

Scaffold 12 can also include a series of perforations 18. Perforations can, for instance, improve fluid exchange between the device 14 and surrounding tissue following implant. Accordingly, perforations 18 can enhance biological acceptance of a device 14 within a patient.

Figure 7A:
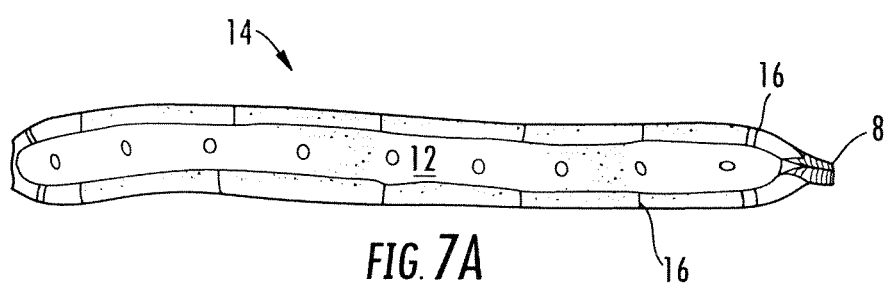
FIG. 7A illustrates a composite implantable device as described herein.
Figure 7B:
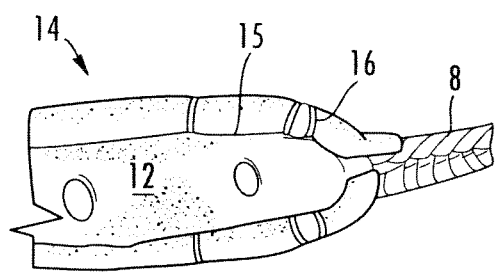
FIG. 7B illustrates a tapered portion of the device of FIG. 7A.

FIGS. 7A and 7B illustrate another embodiment of a composite device 14. As can be seen, composite device 14 includes a scaffold 12 stitched to and overlaying a mechanical reinforcing component (note, the underlying mechanical reinforcing component portion that is beneath scaffold 12 is not is not visible in FIGS. 7A and 7B). In addition to stitches 15 around the periphery of scaffold 12, edge stitches 16 have also been added at the periphery of scaffold 12. In addition, at the tapered ends of scaffold 12, additional edge stitches 16 have been added, so as to better secure scaffold 12 to the underlying component.

It should be understood that while the above described embodiments utilize a series of stitches to affix one or more scaffolds to a mechanical reinforcing component, the use of any one fixation method is not a requirement of the disclosed subject matter. A composite device as described herein can utilize any suitable method for affixing a mechanical reinforcing component to one or more scaffolds. For example, other methods for affixing a mechanical reinforcing component to a scaffold can be utilized including, without limitation, interweaving a scaffold through a portion of a mechanical reinforcing component; the use of a secondary fixation device between a mechanical reinforcing component and a scaffold, e.g., an anchoring device such as a rivet or tack or a secondary material between the two and to which both are affixed; a biocompatible adhesive located between the two that can chemically or physically affix a mechanical reinforcing component to a scaffold; forming a scaffold in the presence of a mechanical reinforcing component such that at least a portion of the component is affixed to and/or encapsulated within the scaffold, for instance crosslinking a natural or synthetic scaffold material in the presence of at least the wide portion of a mechanical reinforcing component such that at least that portion of the mechanical reinforcing component is bonded to the scaffold; and so forth.

In addition, it should be understood that while the illustrated embodiments encompass scaffolds that have been shaped to match a surface area of an underlying component, this is not a requirement of disclosed composite devices. For instance, in other embodiments, a scaffold can overlay only a portion of a wide section of another component. In addition, a scaffold can completely enclose a section of an underlying component, including portions of any narrow extensions that extend from a wider portion of a mechanical reinforcing component. In another embodiment, a scaffold can extend beyond the width of the wider section of an underlying component.

A composite implantable device as disclosed herein can include other components, in addition to a scaffold and a mechanical reinforcing component. For instance, a device can include secondary reinforcement material such as suture along an edge of a device. In one embodiment, a device can include additional functional materials in cooperation with the other components. For example, a device can include an additional device component such as a portion of a replacement joint, anchoring device, or the like in conjunction with a device.

Disclosed composite devices can be provided as sterile or non-sterile devices, depending upon the desired application of a particular device. When considering sterile devices, any sterilization procedures can be utilized as is generally known in the art. For example, disclosed devices can be sterilized by liquid chemical, gas chemical, radiation, or any other sterilization process.

In one embodiment, disclosed devices can be utilized in surgical repair procedures for damaged *human* or animal soft tissues such as, e.g., tendons and ligaments that have been damaged as a consequence of injury, degradation, or disease. For example, composite materials as disclosed herein can be beneficially utilized in surgical procedures including, without limitation, ACL, PCL, MCL, or LCL repair; rotator cuff repair, foot and ankle repair, and the like.

Figure 8A:
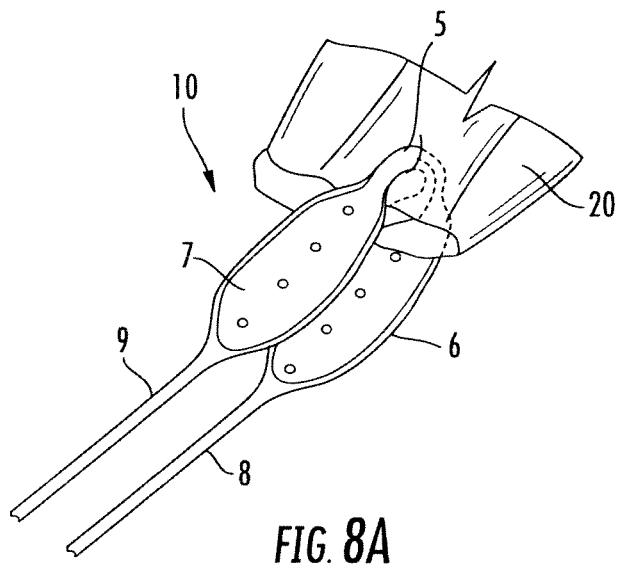
FIG. 8A illustrates a simple stitch method for delivering a composite implantable device as described herein to a damaged or torn soft tissue.

For example, and with reference to FIG. 8, a composite device comprising a mechanical reinforcing component similar to that illustrated in FIG. 4 including two elongated narrow end portions 8, 9, two wide portions 6, 7, and a neck 5 therebetween in combination with a cellular scaffold component affixed to wide portions 6 and 7, can be attached to a tendon end 20 according to various processes. For instance, according to a method as illustrated in FIG. 8A, a simple stitch can be utilized such that one end portion 8 and one wide portion 6 are on a first side of tendon end 20 while the other end portion 9 and wide portion 7 are on the other side of tendon end 20. Neck 5 can be used to accurately locate the center of component 10 in the tendon end 20. In addition, through utilization of a geometry including a narrow neck 5 as illustrated, a smaller portion of component 10 can be located within tendon end 20 following delivery of the device to the repair site.

Figure 8B:
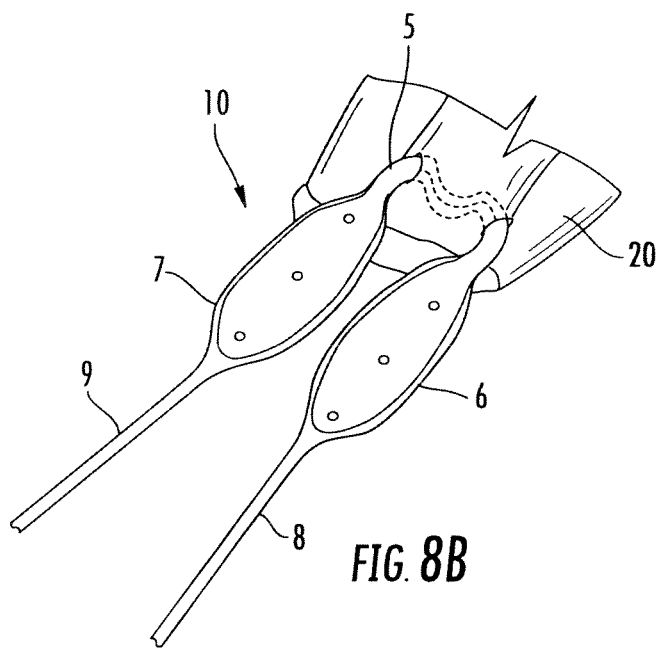
FIG. 8B illustrates an incline mattress stitch method for delivering a composite implantable device as described herein to a damaged or torn soft tissue.

A method as illustrated in FIG. 8B utilizes an inclined mattress stitch that, as illustrated, leaves both ends of the mechanical reinforcing component 10 and the cellular scaffold affixed thereto on the same side of tendon end 20. Neck 5 can be used to accurately locate the center of component 10 in the tendon end 20. In addition, through utilization of a geometry including a narrow neck 5 as illustrated, a smaller portion of component 10 can be located within tendon end 20 following delivery of the device to the repair site. An inclined mattress stitch may be preferred in some embodiments as this stitch has been shown clinically to exhibit better force distribution and less chance of pull out of tendon as compared to a simple stitch when utilizing suture. Accordingly, a mattress or inclined mattress stitch utilizing a device as disclosed herein can exhibit even greater improvement in clinical applications.

Disclosed devices can be used in procedures directed to other tissues including muscles, vascular tissue, synovial tissue, biomembranes such as endocranium, pericardium, pleura, organs, bones, and the like. For instance, disclosed composite devices can be applied to bone in reconstruction or stabilization of a bone or a joint.

Disclosed devices can be utilized in other tissue repair process as well including, e.g., repair of soft tissue defects as in cosmetic and plastic reconstructive surgical procedures. In another embodiment, disclosed devices can be used as suture bolsters for damaged tissue in need thereof such as damaged connective, lung or liver tissue. Devices as disclosed herein can also be useful in supporting damaged organs or components thereof, for example as a support structure for supporting bladder or urethra tissue, for instance in the treatment of incontinence. For instance, disclosed composite devices can be utilized to increase the area of contact, pressure, or the like between tissues or between two areas of a single tissue.

Disclosed processes are provided as examples only, however, and devices as disclosed herein are not intended to be limited to any particular application. For example, disclosed composite devices can be utilized in repair of *human* or animal tissue and in one preferred embodiment, any *human* or animal soft tissue. Disclosed composite devices can beneficially be utilized in repairs involving the increase of vascularity to a tissue or area, in delivering protein rich plasma (PRP), in delivering bone marrow asparate (BMA), in delivering growth factors to a location, and so forth. For instance, a disclosed device can be held in a solution of one or more beneficial compounds, e.g., growth factors, BMA, PRP, and so forth, prior to implantation. Beneficial compounds can diffuse into one or both of a mechanical reinforcement component and a scaffolding component during this time. Following implantation, the beneficial compounds can the diffuse down the new concentration gradient to be delivered into the surrounding implantation area.

Disclosed devices can provide many benefits as compared to suture as has been used previously in similar procedures. For example, disclosed devices can prevent damage to surrounding tissue as has been known to develop when sutures have been used in tissue repair. In addition, due to improved load distribution and increased contact area, the stability of disclosed composite devices can be greater than suture following fixation at a repair site. Moreover, composite devices as disclosed herein are less likely to separate from surrounding tissue following fixation. Thus, composite devices as disclosed herein can exhibit improved adherence to surrounding tissue following fixation thereto without causing further damage to the surrounding tissue. Moreover, disclosed composite devices can do so while encouraging long term repair of the damaged tissue.

Disclosed composite devices can be utilized to provide both short term and long term repair mechanisms to damaged tissue in a single procedure. This can not only reduce surgery time, as separate tissue augmentation processes need not be required in a reconstructive surgery when utilizing disclosed implants, but can also lead to faster recovery time for patients and more complete repair of damaged tissues.

Moreover, features of disclosed composite devices can result in reduced technique variation during use, as disclosed devices can enable surgeons to perform anatomically sound repairs in a consistent manner from procedure to procedure and from surgeon to surgeon. Additionally, disclosed subject matter can provide a route for an increased number of surgeons to incorporate tissue augmentation materials in reconstructive surgeries, and particularly arthroscopic procedures, as it can facilitate delivery of tissue augmentation materials to a repair site.

The disclosed subject matter may be further elucidated with reference to the Examples, set for below. The example is provided by way of explanation of the subject matter, not as limitation thereof.

EXAMPLE 1

A polyetherether ketone (PEEK) woven ribbon was laser cut to form a wide middle section 6 cm in length and 6 mm in width. The wide section was tapered at the ends to narrow into elongated ends 2 mm wide. The overall geometry of the ribbon was similar to that of the embodiment illustrated in FIG. 3, with a total length of approximately 12 inches and the wider 6 cm portion centered within the device. The porosity of the device varied from about 100 µm to about 300 µm.

Two collagen strips were laser cut from crosslinked *equine* pericardium. The strips were cut to approximate the wide middle portion of the cut ribbon, i.e., 6 cm in length and 6 mm in width with tapered ends.

A collagen strip was located on either side of the wide middle section of the PEEK ribbon and affixed with a simple stitch around the perimeter. Stitches were formed with #5-0 braided polyester suture.

The tensile strength of the formed composite device was examined using an automated tensile test machine. Tensile strength was found to be 249N.

EXAMPLE 2

A woven component was formed from PEEK multi-filament yarns with 41 total ends. The component was shaped to contain a wide central portion with narrow extensions. The dimensions of the wide portion of the component were 6 cm in length with a width of 6 mm tapering to 2 mm at each end. The narrow extensions of the component were 2 mm in width, and the overall length of the component was approximately 30 in. The porosity of the woven component in the wide central region varied from about 200 µm to about 400 µm.

Two collagen strips were laser cut from crosslinked *equine* pericardium. The strips were cut to approximate the wide middle portion of the component, i.e., 6 cm in length and 6 mm in width with tapered ends. Perforations were laser cut along the center axis of each collagen strip. The perforations were spaced approximately 6 mm apart and were approximately 0.5 mm in diameter.

A collagen strip was located on either side of the wide middle section of the PEEK component and affixed with a simple stitch around the perimeter. Stitches were formed with #5-0 braided polyester suture as described previously. Six additional edge stitches were added to each end of the wide portion of the component. The addition of the edge stitches lowered the overall profile of the composite structure at these ends.

The tensile strength of the formed composite device was examined using an automated tensile test machine. Tensile strength was found to be 279N.

EXAMPLE 3

A woven component was formed from PEEK multi-filament yarns with 66 total ends. The component was shaped to contain a wide central portion with narrow extensions. The dimensions of the wide portion of the component were 6 cm in length with a width of 6 mm tapering to 2 mm at each end. The narrow extensions of the component were 2 mm in width, and the overall length of the component was approximately 30 in. The porosity of the woven component in the wide central region varied from about 20 μm to about 100 μm.

Two collagen strips were laser cut from crosslinked *equine* pericardium. The strips were cut to approximate the wide middle portion of the component, i.e., 6 cm in length and 6 mm in width with tapered ends.

A collagen strip was located on either side of the wide middle section of the PEEK component and affixed with a simple stitch around the perimeter. Stitches were formed with #5-0 braided polyester suture as described previously. Six additional edge stitches were added to each end of the wide portion of the component. The addition of the edge stitches lowered the overall profile of the composite structure at these ends.

The tensile strength of the formed composite device was examined using an automated tensile test machine. Tensile strength was found to be 358N.

EXAMPLE 4

A woven component was formed from PEEK multi-filament yarns with 82 total ends. The component was shaped to contain a wide central portion with narrow extensions. Further, the wide central portion was configured with two wide portions separated by a narrower middle neck section. The dimensions of each of the wide portions of the component were 8 cm in length and 8 mm in width. The neck section of the component between the two wide portions was 1 cm in length and 4 mm in width. The narrow extensions at either end of the component were 2 mm in width, and the overall length of the component was approximately 30 in. Additionally, in this particular example, the narrow extensions were tubular in shape. The porosity of the woven component in the wide central region varied from about 20 μm to about 100 μm.

Two collagen strips were laser cut from crosslinked *equine* pericardium. The strips were cut to approximate the wide central portion of the component, i.e., 8 cm in length and 6 mm in width with a 1 cm middle neck section and tapered ends.

A collagen strip was located on either side of the wide middle section of the PEEK component and affixed with a simple stitch around the perimeter. Stitches were formed with #5-0 braided polyester suture as described previously.

The tensile strength of the formed composite device was examined using an automated tensile test machine. Tensile strength was found to be 429N.

EXAMPLE 5

A woven component was formed from High Tenacity Polyester (HTPET) multi-filament yarns with 66 total ends. The component was shaped to contain a wide central portion with narrow extensions. The dimensions of the wide portion of the component were 8 cm in length with a width of 6 mm tapering to 3 mm at each end. The narrow extensions of the component were 3 mm in width, and the overall length of the component was approximately 30 in. The porosity of the component varied from about 20 μm to about 100 μm.

Two collagen strips were laser cut from crosslinked *equine* pericardium. The strips were cut to approximate the wide middle portion of the component, i.e., 8 cm in length and 6 mm in width with tapered ends.

A collagen strip was located on either side of the wide middle section of the HTPET component and affixed with a simple stitch around the perimeter. Stitches were formed with #5-0 braided polyester suture as described previously.

The tensile strength of the formed composite device was examined using an automated tensile test machine. Tensile strength was found to be 536N.

EXAMPLE 6

Components were formed similar to those illustrated in FIG. 3 from PEEK multifilament yarns. The number of yarn ends was varied, and the porosity and strength characteristics were determined for each material. Results are shown in Tables 1 and 2, below.

TABLE 1

Porosity (μm) vs. Number of yarn ends

| Total yarn ends | Porosity range (μm) |
|---|---|
| 41 | 200-400 |
| 66 | 50-100 |

TABLE 2

Tensile strength vs. Number of yarn ends

| Total yarn ends | Tensile Strength (N) |
|---|---|
| 41 | 279 |
| 66 | 358 |
| 82 | 429 |

As can be seen, variation in the number of yarn ends, can affect the tensile strength and porosity of the component.

EXAMPLE 7

Two composite devices as described above in Example 2 were utilized in carrying out a rotator cuff repair as illustrated in FIGS. 9A-9D.

Figure 9A:
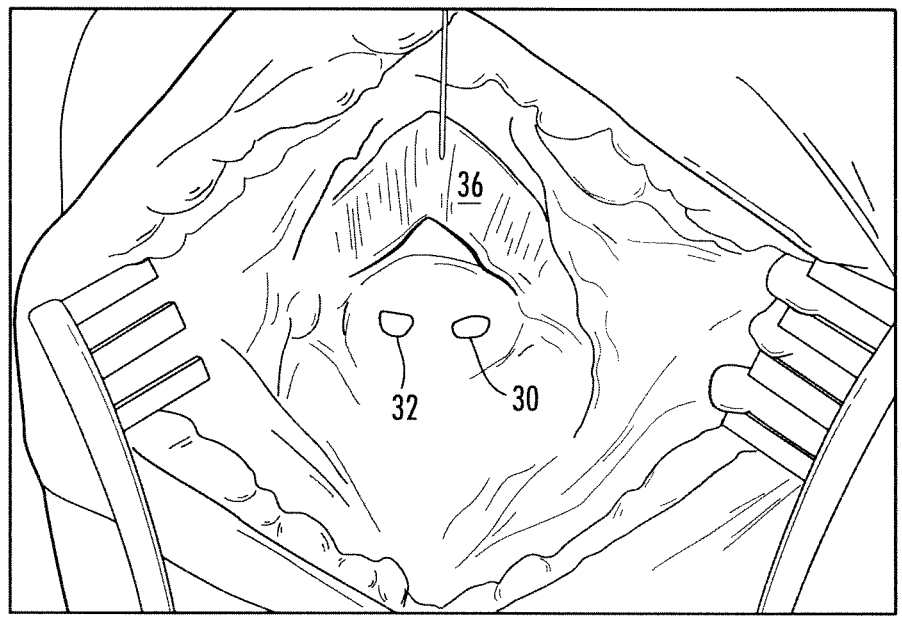
FIGS. 9A-D illustrate a rotator cuff repair process utilizing a composite implantable device as described herein.
Figure 9B:
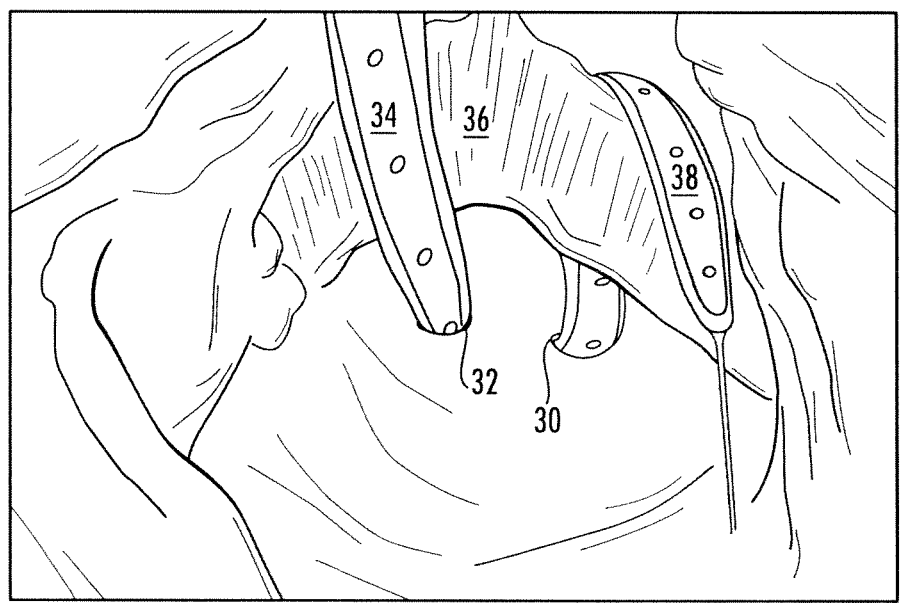
Figure 9C:
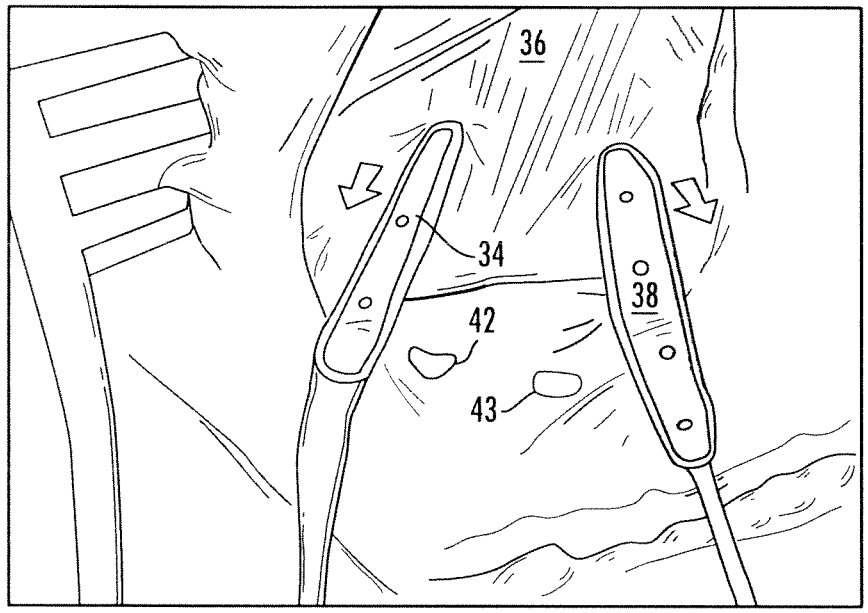
Figure 9D:
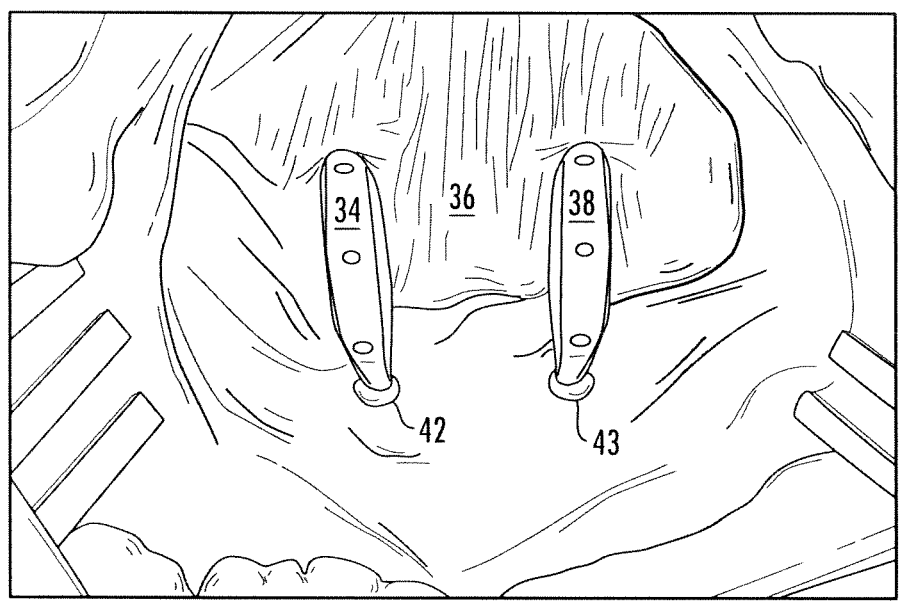

Initially, pilot holes 30, 32 were punched near the articular margin to receive the tissue attachment devices and fixation devices (FIG. 9A). A tissue attachment device 34 was fixated into one of the formed holes 30 using a compression fit fixation device (not shown) (FIG. 9B). The device was then shuttled through the rotator cuff 36 using a suture passer (FIG. 9C). The process was repeated with the second device 38 and the second pilot hole 32. Following insertion, both tissue attachment devices 34, 38 were then pulled laterally to approximate the rotator cuff 36 to the bony insertion site (FIG. 9D). Two holes were created lateral to the greater tuberosity 42, 43. The repair was completed with the fixation of both devices into the lateral holes using compression fit fixation devices (not shown) (FIG. 9D).

It will be appreciated that the foregoing examples, given for purposes of illustration, are not to be construed as limiting the scope of this disclosure. Although only a few exemplary embodiments have been described in detail above, those skilled in the art will readily appreciate that many modifications are possible in the exemplary embodiments without materially departing from the novel teachings and advantages of this disclosure. Accordingly, all such modifications are intended to be included within the scope of the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. A composite implantable tissue attachment device comprising:
   a) a mechanical reinforcing component made of woven fibers, consisting of:
      i. a central portion defining a length, a first width, and a depth, wherein the first width is at least about 1 millimeter along at least a portion of the length and the depth is less than the first width, at least a portion of the central portion defining a porosity; and
      ii. a single first terminal portion and a single second terminal portion; and
   b) a first planar cellular scaffold component that overlays the central portion but not the first and second terminal portions of the mechanical reinforcing component; and
   c) a second planar cellular scaffold component that overlays the central portion but not the first and second terminal portions of the mechanical reinforcing component;
   wherein the first and second cellular scaffold components are shaped to match the shape of the central portion of the mechanical reinforcing component, the first and second cellular scaffold components are secured to a portion of a periphery of the reinforcing component by stitching such that the portion of periphery of the reinforcing component is stitched to a periphery of the first and second cellular scaffold components and the first and second cellular scaffold components are discrete and layered directly upon opposite sites of the mechanical reinforcing component.

2. The composite implantable tissue attachment device of claim 1, wherein the first terminal portion of the mechanical reinforcing component defines a second width, wherein the second width is less than the first width.

3. The composite implantable tissue attachment device of claim 2, wherein the first width of the mechanical reinforcing component tapers in transition to the second width.

4. The composite implantable tissue attachment device of claim 1, wherein the second terminal portion of the mechanical reinforcing component defines a second width that is less than the first width.

5. The composite implantable tissue attachment device of claim 1, wherein the first and second terminal portions of the mechanical reinforcing component define a round cross section.

6. The composite implantable tissue attachment device of claim 1, wherein the mechanical reinforcing component comprises multiple lengths of said central portion, wherein the multiple lengths are separated from one another by lengths of a neck.

7. The composite implantable tissue attachment device of claim 1, wherein the first and second cellular scaffold components are collagen scaffolds.

8. The composite implantable tissue attachment device of claim 7, wherein the collagen scaffolds comprise crosslinked collagen.

9. The composite implantable tissue attachment device of claim 8, wherein the crosslinked collagen scaffolds are non-glutaraldehyde processed collagen scaffolds.

10. The composite implantable tissue attachment device of claim 8, wherein the collagen scaffolds comprise crosslinked reconstituted collagen.

11. The composite implantable tissue attachment device of claim 1, wherein the first and second cellular scaffold components comprise a hydrogel.

12. The composite implantable tissue attachment device of claim 1, wherein the first and second cellular scaffold components overlay the entire length of the central portion of the mechanical reinforcing component.

13. The composite implantable tissue attachment device of claim 1, wherein the first and second cellular scaffold components overlay a portion of the length of the central portion of the mechanical reinforcing component.

14. The composite implantable tissue attachment device of claim 1, wherein the fibers of the mechanical reinforcing component are polymeric fibers.

15. The composite implantable tissue attachment device of claim 14, wherein the polymeric fibers comprise polyetheretherketone.

16. The composite implantable tissue attachment device of claim 14, wherein the polymeric fibers comprise an absorbable polymer.

17. The composite implantable tissue attachment device of claim 1, wherein the fibers are monofilament fibers.

18. The composite implantable tissue attachment device of claim 1, wherein the fibers are multifilament fibers.

19. The composite implantable tissue attachment device of claim 1, the mechanical reinforcing component comprising a plurality of different fibers.

20. The composite implantable tissue attachment device of claim 1, at least a portion of the mechanical reinforcing component defining a porosity less than about 1000 micrometers.

21. The composite implantable tissue attachment device of claim 1, wherein the at least a portion of the length of the mechanical reinforcing component defining the first width has an average pore size of less than about 100 micrometers.

22. The composite implantable tissue attachment device of claim 1, wherein the mechanical reinforcing component is a knit.

23. The composite implantable tissue attachment device of claim 1, wherein the mechanical reinforcing component comprises a braided component.

24. The composite implantable tissue attachment device of claim 1, where the tensile strength of said composite implantable tissue attachment device is greater than about 20 N.

25. The composite implantable tissue attachment device of claim 1, where the tensile strength of said composite implantable tissue attachment device is between about 100 N and about 5000 N.

26. The composite implantable tissue attachment device of claim 1, wherein the device is sterile.

27. A method of repairing a tissue comprising:
passing a first length of a composite implantable tissue attachment device through a first tissue, the composite implantable tissue device comprising:
a) a mechanical reinforcing component made of woven fibers, consisting of:
   i. a central portion defining a length, a first width, and a depth, wherein the first width is at least about 1 millimeter along at least a portion of the length and the depth is less than the first width, at least a portion of the central portion defining a porosity; and
   ii, a single first terminal portion and a single second terminal portion; and
b) a first planar cellular scaffold component that overlays the central portion but not the first and second terminal portions of the mechanical reinforcing component, and
c) a second planar cellular scaffold component that overlays the central portion but not the first and second terminal portions of the mechanical reinforcing component;
wherein the first and second cellular scaffolds components are shaped to match the shape of the central portion of the mechanical reinforcing component, the first and second cellular scaffold components are secured to a portion of a periphery of the reinforcing component by stitching such that the portion of the periphery of the reinforcing component is stitched to a periphery of the first and second cellular scaffold components and the first and second cellular scaffold components are discrete and layered directly upon opposite sites of the mechanical reinforcing component; and
attaching the composite implantable tissue attachment device to a second tissue.

28. The method according to claim 27, wherein the first tissue and the second tissue are different tissues.

29. The method according to claim 27, wherein the first tissue and the second tissue are different areas of the same tissue.

30. The method according to claim 27, wherein at least one of the first tissue and the second tissue is a soft tissue.

31. The method according to claim 30, wherein the soft tissue is human soft tissue.

32. The method according to claim 27, wherein the first tissue is a ligament or a tendon.

33. The method according to claim 27, wherein the first tissue is bone.

34. The method according to claim 27, wherein the first tissue is cartilage.

35. The method according to claim 27, wherein the composite implantable tissue attachment device is attached to the second tissue such that the first or second cellular scaffold component is in contact with at least one of the first tissue and the second tissue.

36. A method according to claim caini 27, wherein the repair comprises restoring a soft tissue to bone insertion site.

37. The method according to claim 27, wherein the repair comprises increasing contact area between the first tissue and the second tissue.

38. The method according to claim 27, wherein the repair comprises increasing pressure between the first tissue and the second tissue.

39. The method according to claim 27, wherein the repair comprises the delivery of a cellular scaffold.

40. A method according to claim 27, wherein the cellular scaffold comprises collagen.

41. A method according to claim 27, wherein the repair comprises increasing vascularity.

42. A method according to claim 27, wherein the composite implantable tissue attachment device is utilized to deliver at least one of protein rich plasma, bone marrow aspirate and growth factors.

* * * * *